United States Patent
Manzer et al.

(10) Patent No.: US 6,762,333 B1
(45) Date of Patent: *Jul. 13, 2004

(54) PROCESS FOR REDUCING THE FLUORINE CONTENT OF HYDROFLUOROCARBONS AND HYDROHALOFLUOROCARBONS

(75) Inventors: Leo Ernest Manzer, Wilmington, DE (US); V. N. Mallikarjuna Rao, Wilmington, DE (US); Steven Henry Swearingen, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/460,023

(22) Filed: Jun. 2, 1995

Related U.S. Application Data

(63) Continuation of application No. 08/112,750, filed on Aug. 25, 1993, now Pat. No. 5,523,498, which is a continuation-in-part of application No. 07/987,529, filed on Dec. 8, 1992, now abandoned.

(51) Int. Cl.$^7$ .............................................. C07C 25/13
(52) U.S. Cl. ..................................................... 570/123
(58) Field of Search ................................ 570/123, 166, 570/168, 156

(56) References Cited

U.S. PATENT DOCUMENTS

| | | | |
|---|---|---|---|
| 3,193,587 A | 7/1965 | Baranauckas et al. | 260/648 |
| 3,541,165 A | 11/1970 | Vecchio et al. | 260/653.4 |
| 3,632,834 A | 1/1972 | Christopher, Jr. | 260/653.7 |
| 3,754,043 A | 8/1973 | Bjornson et al. | 260/653 |
| 4,766,260 A | 8/1988 | Manzer et al. | 570/168 |
| 4,902,838 A | 2/1990 | Manzer et al. | 570/151 |
| 5,036,036 A | 7/1991 | Lerou | 502/317 |
| 5,132,473 A | 7/1992 | Furutataka et al. | 570/123 |
| 5,171,899 A | 12/1992 | Furutaka et al. | 570/123 |
| 5,177,271 A | 1/1993 | Elsheikh et al. | 570/156 |
| 5,345,017 A | 9/1994 | Rao et al. | 570/227 |

FOREIGN PATENT DOCUMENTS

| | | | |
|---|---|---|---|
| CA | 705456 | 3/1965 | 260/648 |
| CA | 2025145 | 3/1991 | C07C/17/20 |
| EP | 0 407 711 | 1/1991 | C07C/21/18 |
| EP | 0 514 920 | 11/1992 | C07C/17/20 |

OTHER PUBLICATIONS

Vecchio, M. et al, "Studies on a Vapour–Phase Process for the Manufacture of Chlorofluoroethanes", *J. Fl. Chem.*, 4, 117–139 (1974).

Stull, D.R., *The Chemical Thermodynamics of Organic Compounds*, John Wiley & Sons, Inc., NY, pp. 226; 498; 502 (1969).

Adams, R. et al, (eds.), *Organic Reactions vol. II*, p. 56 (1944).

*Ullmann's Encyclopedia of Industrial Chemistry*, A6, 461–462 (1986).

Manzer, L.E., "The CFC–Ozone Issue: Progress on the Development of Alternatives of CFCs", *Science*, 249, 31–35 (1990).

Hudlicky, M., *Chemistry of Organic Fluorine Compounds*, pp. 228–232 (1992).

*Primary Examiner*—Samuel Barts
*Assistant Examiner*—Elvis O. Price

(57) ABSTRACT

The fluorine content of an acyclic saturated compound of the formula $C_nF_aX_bH_c$ (wherein each X is independently selected from the group consisting of Cl and Br, and wherein n is 1 to 6, a is 1 to 13, b is 0 to 12, c is 1 to 9, and a+b+c equals 2n+2) is reduced by reacting the acyclic saturated compound with HCl in the vapor phase at an elevated temperature in the presence of a catalyst, the mole ratio of HCl to the acyclic saturated compound being at least about 1:1.

16 Claims, No Drawings

US 6,762,333 B1

PROCESS FOR REDUCING THE FLUORINE CONTENT OF HYDROFLUOROCARBONS AND HYDROHALOFLUOROCARBONS

This is a continuation of application Ser. No. 08/112,750, filed Aug. 25, 1993 now U.S. Pat. No. 5,523,490 which is a continuation-in-part of application Ser. No. 07/987,529, filed Dec. 8, 1992 now abandoned.

FIELD OF THE INVENTION

This invention relates to halogen-substituted hydrocarbons containing fluorine, and more particularly, to a process for reducing the fluorine content of hydrofluorocarbons and hydrohalofluorocarbons.

BACKGROUND

Hydrofluorocarbons (i.e., compounds containing only the elements carbon, fluorine, and hydrogen) and hydrohalofluorocarbons (i.e., compounds containing only the elements carbon, fluorine, hydrogen and chlorine and/or bromine) are widely used as refrigerants, aerosol propellants, blowing agents, cleaning agents, fire extinguishants and chemical intermediates. Commercially, many of such compounds are prepared by the reactions of hydrogen fluoride with olefins or saturated compounds containing chlorine. Some compounds (e.g., various hydrofluorocarbons) can be prepared by the hydrogenolysis of an appropriate chlorine and/or bromine-containing precursor. These processes can also produce halogenated hydrocarbons having a lesser commercial value and/or not having the desired properties. Furthermore, the supply/demand situation for any particular product can vary and there may be an oversupply of a particular hydrofluorocarbon or hydrohalofluorocarbon. For environment al reasons, it may not be advantageous to dispose of surplus or by-products by such methods as incineration, but rather to further react these materials to increase the yields of useful products. A reduction of the fluorine content of various hydrofluorocarbons and hydrochlorofluorocarbons can improve their value as commercial products and/or as precursors for producing other useful products.

SUMMARY OF THE INVENTION

This invention provides a method for reducing the fluorine content of an acyclic saturated compound of the formula $C_nF_aX_bH_c$ wherein each X is independently selected from the group consisting of Cl and Br, and wherein n is 1 to 6, a is 1 to 13, b is 0 to 12, c is 1 to 9, and a+b+c equals 2n+2. The method comprises the step of reacting the acyclic saturated compound with HCl in the vapor phase at an elevated temperature in the presence of a catalyst, the mole ratio of HCl to the acyclic saturated compound being at least about 1:1.

DETAILED DESCRIPTION

The present invention provides a process for reducing the fluorine content of an acyclic saturated compound of the formula $C_nF_aX_bH_c$ wherein each X is independently selected from Cl and Br, and wherein n is 1 to 6, a is 1 to 13, b is 0 to 12, c is 1 to 9, and a+b+c equals 2n+2, by reacting the acyclic saturated compound with HCl in the vapor phase in the presence of a catalyst. Of particular note are embodiments of the invention where n is 1, embodiments of the invention where n is 2, and embodiments of the invention where n is 3. Where n is 2 or more, the reaction products having reduced fluorine content may include saturated and/or olefinic compounds. For example, $CH_3CF_3$ may be reacted to produce saturated compounds (e.g., $CH_3CClF_2$ and $CH_3CCl_2F$) and unsaturated compounds (e.g., $CH_2=CF_2$, $CH_2=CClF$ and $CH_2=CCl_2$).

Included in this invention is the reaction of an acyclic saturated compound of the formula $C_nF_aX_bH_c$ wherein n is at least 2, c is at least 2 and the mole ratio of HCl to the compound is at least about 5:1 to produce a hydrogen-containing olefinic product. Also included is the reaction of an acyclic saturated compound of the formula $C_nF_aX_bH_c$ wherein n is 2, c is 1 and the mole ratio of HCl to the compound is at least about 5:1 to produce a perhalogenated olefinic product. For example, $CF_3CF_2H$ may be reacted with HCl (preferably in a molar ratio of $HCl:CF_3CF_2H$ of at least about 6:1) in the presence of a catalyst (e.g., an aluminum fluoride catalyst) to produce $CCl_2=CCl_2$ as the major halogenated hydrocarbon reaction product. Also included is the reaction of an acyclic saturated compound of the formula $C_nF_aX_bH_c$ where n is at least 2 (e.g., n is 2 or n is 3) and the mole ratio of HCl to the compound is about 5:1 or less (e.g., from 2:1 to 5:1) at an elevated temperature less than about 350° C. (e.g., 250° C. to 325° C.) to produce compounds of reduced fluorine content which are primarily (i.e., more than 50 mole percent) saturated compounds. Other embodiments involve the reaction of an acyclic saturated compound of the formula $CF_aX_bH_c$ wherein b is 0 to 2.

The invention includes reactions of HCl with mixtures of compounds of the formula $C_nF_aX_bH_c$ with each other and/or with other organic compounds such as ethers (e.g., dimethylether), alcohols (e.g., methanol) and hydrocarbons (e.g., propane and/or cyclohexane). In some embodiments, the mixtures are azeotropic. Examples of acyclic saturated compounds which may be reacted with HCl in accordance with this invention include $CH_2FCF_3$, $CHF_3$, $CHF_2CF_3$, $CH_3CF_3$, $CH_3CHF_2$, $CHCl_2F$, $CHClF_2$, $CHCl_2CF_3$, $CHClFCF_3$, $CH_2ClCF_3$, $CH_3CF_2Cl$, $CHBrF_2$ and $CF_3CHBrF$.

Chlorine may be present in some process embodiments, either as an initial reactant or as an in-situ formed product. Of note are reactions wherein $Cl_2$ is present during the reaction and a perhalogenated product is produced.

Suitable catalysts which can be used for reducing the fluorine content of the starting materials by reaction with HCl include vapor phase fluorination catalysts. Catalysts which may be used in accordance with this invention include metals (including elemental metals, metal oxides and/or other metal salts); alumina; fluorided alumina; aluminum fluoride; metals on alumina; metals on aluminum fluoride; magnesium fluoride on aluminum fluoride; metals on fluorided alumina; alumina on carbon; aluminum fluoride on carbon; fluorided alumina on carbon; metals on carbon; chromium catalysts (e.g., $Cr_2O_3$ by itself or with other metals such as Mg and/or Zn); mixtures of metals, aluminum fluoride, and graphite; and chromium-magnesium optionally on graphite. Suitable metals for use as catalysts (optionally on alumina, aluminum fluoride, fluorided alumina or carbon) include chromium, Group VIII metals (iron, cobalt, nickel, ruthenium, rhodium, palladium, osmium, iridium, platinum), Group VIIB metals (manganese, rhenium), Group IIIB metals (scandium, yttrium, lanthanum), Group IB metals (copper, silver, gold), zinc and/or metals having an atomic number of 58 through 71 (cerium, praseodymium, neodymium, promethium, samarium, europium, gadolonium, terbium, dysprosium, holmiun, eribum, thulium, ytterbium or lutetium). Preferably, when used with a support, the total metal content of the catalyst will be from about 0.1 to 20 percent by weight; typically, from about 0.1 to 10 percent by weight.

Fluorided alumina and aluminum fluoride can be prepared as described in U.S. Pat. No. 4,902,838. Metals on aluminum fluoride and metals on fluorided alumina can be prepared by procedures described in U.S. Pat. No. 4,766,260. Catalysts comprising chromium are well known in the art (see e.g., U.S. Pat. No. 5,036,036). Chromium supported on alumina can be prepared as described in U.S. Pat. No. 3,541,165. Chromium supported on carbon can be prepared as described in U.S. Pat. No. 3,632,834. Catalysts comprising chromium and magnesium may be prepared as described in Canadian Patent No. 2,025,145. Other metals and magnesium optionally on graphite can be prepared in a similar manner to the latter patent. Preferred catalysts include catalysts comprising aluminum fluoride and catalysts comprising chromium oxide.

Weak catalysts for this reaction such as silicon carbide may also be used.

The reaction of the acyclic saturated compound of the formula $C_nF_aX_bH_c$ with HCl in the presence of the catalysts of the instant invention is suitably conducted at a temperature within the range of from about 250° C. to 450° C., preferably from about 300° C. to 400° C., and most preferably from about 325° C. to about 375° C. The contact time is typically from about 1 to about 120 seconds, preferably from about 5 to about 60 seconds.

The amount of HCl should be at least a stoichiometric amount. Generally, the molar ratio of HCl to the acyclic saturated compound can range from about 1:1 to about 100:1, preferably about 3:1 to 50:1, and more preferably about 5:1 to 20:1.

In general, with a given catalyst composition, the higher the temperature and the longer the contact time, the greater is the conversion of fluorinated products and the greater is the production of polychlorinated products. The above variables can be balanced, one against the other, so that the formation of lower fluorine substituted products is maximized.

The reaction products may normally be separated by conventional techniques, such as distillation. Some of the reaction products will have desired properties for commercial use by themselves, or as intermediates for making other commercial products. Others, such as $CHCl=CCl_2$, $CCl_2=CCl_2$, $CHCl_3$, etc. can be recycled back to reactors which are being used for the synthesis of hydrofluorocarbons and hydrohalofluorocarbons. For example, vapor-phase processes for manufacturing $CF_3CHCl_2$ and/or $CF_3CHFCl$ by hydrofluorination of $CCl_2=CCl_2$ often produce substantial amounts of $CF_3CF_2H$ by-product; and the process of this invention may be used to obtain $CCl_2=CCl_2$ (and HF) for use as starting materials for the hydrofluorination. The process of this invention provides a method of utilizing substantially all of a halogenated hydrocarbon plant's products. This utility has the benefit of providing a manufacturing facility with minimum waste, and therefore, minimum environmental impact.

The reaction of the acyclic saturated compound with HCl may be conducted in any suitable reactor, including fixed and fluidized bed reactors. The reaction vessel should be constructed from materials which are resistant to the corrosive effects of hydrogen fluoride such as Inconel™ nickel alloy and Hastelloy™ nickel alloy.

Pressure is not critical. Atmospheric and superatmospheric pressures are the most convenient and are therefore preferred.

Practice of the invention will become further apparent from the following non-limiting examples.

EXAMPLES

In the following illustrative examples, all parts are by weight, all percentages are molar, and all temperatures are Celsius unless otherwise stated.

General Procedure for Fluorided Alumina Catalyst

A reactor (a 0.5 inch (1.3 cm) ID, 12 inch (30.5 cm) long Inconel™ nickel alloy pipe) was charged with the amount of catalyst as described in the following examples, and placed in a sand bath. The bath was gradually heated to 400° C. while $N_2$ gas at a flow rate of 50 cc/min was passed through the reactor to remove traces of water. The temperature was lowered to 200° C. and HF and $N_2$ gas (1:4 molar ratio) were passed through the reactor. The $N_2$ flow was decreased with time until neat HF was being passed through the reactor. At this point the temperature was gradually raised to 450° C. and maintained there for 15 to 300 minutes. X-ray diffraction analysis showed that the catalyst support was converted to essentially all aluminum fluoride.

The temperature was then decreased to the indicated value and, thereafter, the other reactant flows were started. The flows were adjusted to give the indicated molar ratios and contact times in the Examples.

The reactor effluent was sampled on-line with a Hewlett Packard HP 5890 gas chromatograph using a 20 foot (6.1 m) long, one-eighth inch (3.2 mm) diameter column containing Krytox® perfluorinated polyether on an inert support, and a helium flow of 35 cc/min. Gas chromatographic conditions were 70° C. for three minutes followed by temperature programming to 180° C. at a rate of 6° C./minute.

Example 1

Reaction of Pentafluoroethane and HCl

The General Procedure for Fluorided Alumina Catalyst was followed using 19.9 g (30 mL) of $COCl_2/Al_2O_3$ (2% Co) as the initial catalyst charge. The $HCl:CHF_2CF_3$ (HFC-125) molar ratio was varied from 2:1 to 20:1, the reaction temperature was varied from 200 to 450° C., and the contact time (C.T.) was varied from 30 to 60 seconds. The results of these runs are shown in Table 1.

TABLE 1

| T °C. | Molar Ratio | C.T. Sec | % 125[a] | % 115[b] | % 124[c] | % 114a[d] | % 123[e] | % 1111[f] | % 1120[g] | % PCE[h] |
|---|---|---|---|---|---|---|---|---|---|---|
| 200 | 20:1 | 30 | 95.8 | 0.5 | 1.7 | 0.0 | 0.8 | 0.0 | 0.0 | 0.0 |
| 250 | 20:1 | 30 | 89.9 | 0.4 | 3.6 | 0.0 | 5.1 | 0.1 | 0.0 | 0.3 |
| 300 | 20:1 | 30 | 73.7 | 0.4 | 4.6 | 0.0 | 13.9 | 1.0 | 0.1 | 6.1 |
| 350 | 20:1 | 30 | 49.4 | 0.3 | 4.0 | 0.1 | 15.2 | 3.4 | 0.2 | 27.0 |
| 350 | 12:1 | 30 | 47.0 | 0.3 | 4.2 | 0.1 | 14.6 | 2.3 | 0.2 | 30.7 |
| 350 | 2:1 | 30 | 62.9 | 0.3 | 6.3 | 0.1 | 15.4 | 1.3 | 0.2 | 13.0 |
| 400 | 20:1 | 30 | 23.8 | 0.2 | 2.4 | 0.2 | 7.6 | 4.9 | 0.8 | 59.3 |
| 400 | 12:1 | 30 | 22.7 | 0.3 | 2.6 | 0.3 | 7.8 | 4.1 | 1.0 | 60.5 |
| 400 | 10:1 | 60 | 13.7 | 0.5 | 2.2 | 0.4 | 7.1 | 4.4 | 2.1 | 68.9 |
| 425 | 12:1 | 30 | 13.5 | 0.5 | 1.8 | 0.3 | 5.2 | 5.4 | 1.6 | 70.8 |
| 425 | 10:1 | 60 | 8.3 | 1.0 | 1.8 | 0.4 | 5.7 | 6.3 | 3.7 | 71.6 |
| 425 | 6:1 | 30 | 22.5 | 0.5 | 3.9 | 0.3 | 9.9 | 6.5 | 2.0 | 51.9 |

TABLE 1-continued

| T °C. | Molar Ratio | C.T. Sec | % 125[a] | % 115[b] | % 124[c] | % 114a[d] | % 123[e] | % 1111[f] | % 1120[g] | % PCE[h] |
|---|---|---|---|---|---|---|---|---|---|---|
| 450 | 20:1 | 30 | 7.1 | 0.3 | 0.8 | 0.2 | 2.0 | 5.2 | 2.0 | 81.9 |
| 450 | 12:1 | 30 | 7.9 | 0.7 | 1.2 | 0.3 | 3.4 | 6.9 | 2.6 | 76.0 |

[a]125 is $CHF_2CF_3$
[b]115 is $CClF_2CF_3$
[c]124 is $CF_3CHClF$
[d]114a is $CF_3CCl_2F$
[e]123 is $CF_3CHCl_2$
[f]1111 is $CClF=CCl_2$
[g]1120 is $CHCl=CCl_2$
[h]PCE is $CCl_2=CCl_2$

Example 2

Reaction of Pentafluoroethane and HCl

A ⅝" (1.6 cm) I.D. Inconel™ nickel alloy reactor was charged with chrome oxide (60 mL, 78 g, 12/20 mesh (1.7 to 0.84 mm)) and heated to 275° C. in a flow of nitrogen (25 cc/min) for about 20 hours. The temperature was reduced to 175° C. and a 2:1 molar ratio of nitrogen and HF was started through the reactor (total flow 100 mL/min). After one hour under these conditions, the molar ratio of nitrogen to HF was adjusted to 1:3 and the temperature increased gradually over a two hour period to 400° C. The reactor was then brought back to the desired operating temperature, the flow of HF and nitrogen stopped and the flow of reactants started. The $CHF_2CF_3$ (HFC-125)/HCl molar ratio was 1/5, the contact time was 60 seconds and the reaction temperatures were as shown in Table 2.

TABLE 2

| T °C. | % 125 | % 115 | % 124 | % 133a[a] | % 114[b] | % 114a | % 123 | % 1120 | % PCE | % Other[c] |
|---|---|---|---|---|---|---|---|---|---|---|
| 280 | 54.0 | 0.0 | 4.4 | 0.1 | 0.0 | 0.0 | 36.4 | 0.1 | 4.6 | 0.4 |
| 300 | 32.6 | 0.0 | 7.8 | 0.3 | 0.0 | 0.3 | 45.0 | 0.3 | 12.7 | 1.0 |
| 340 | 18.3 | 4.7 | 10.3 | 4.0 | 0.8 | 2.7 | 30.8 | 2.9 | 22.4 | 2.9 |
| 360 | 13.3 | 14.3 | 7.3 | 6.1 | 1.1 | 2.8 | 19.5 | 7.5 | 23.6 | 4.5 |

[a]133a is $CF_3CH_2Cl$
[b]114 is $CClF_2CClF_2$
[c]includes $CF_3CH_3$ and $CCl_2=CClF$ Example 3

Reaction of $CHClFCF_3$ and HCl

A reactor (a 0.5 inch (1.3 cm) ID, 12 inch (30.5 cm) long Inconel™ nickel alloy pipe) was charged with 23.1 g (30 mL) of $CrCl_3$/carbon (29% $CrCl_3$). The catalyst was dried in a nitrogen stream at 300° C. prior to use. The HCl:CHClFCF₃ (HCFC-124) molar ratio was 6:1, the reaction temperature was 350° C., and the contact time was 30 seconds. The result of this run is shown in Table 3.

TABLE 3

| % 125 | % 124 | % 114a | % 123 | % 1111 | % PCE |
|---|---|---|---|---|---|
| 3.2 | 24.8 | 3.4 | 62.8 | 0.5 | 1.5 |

Example 4

Reaction of $CH_2ClCF_3$ and HCl

The reactor, catalyst and procedure were the same as those of Example 3. The HCl:$CH_2ClCF_3$ (HCFC-133a) molar ratio was 6:1, the reaction temperature was 350° C., and the contact time was 30 seconds. The result of this run is shown in Table 4 in area %.

TABLE 4

| % 143a | % 133a | % 123 | % 1121[a] | % 1120 | % PCE |
|---|---|---|---|---|---|
| 1.7 | 60.7 | 1.0 | 2.6 | 28.6 | 3.7 |

[a]1121 is $C_2HCl_2F$

Example 5

Reaction of $CHCl_2CF_3$ and HCl

The reactor, catalyst and procedure were the same as those of Example 3. The HCl:$CHCl_2CF_3$ (HCFC-123) molar ratio was 6:1, the reaction temperature was 350° C., and the contact time was 30 seconds. The result of this run is shown in Table 5 in area %.

TABLE 5

| % 123a[a] | % 123 | % 113a | % 122 | % 1111 | % 1120 | % PCE |
|---|---|---|---|---|---|---|
| 2.1 | 91.7 | 0.9 | 1.0 | 0.8 | 0.9 | 1.2 |

[a]123a is $CHClFCCl_2$

Example 6

Reaction of $CH_2FCF_3$ and HCl

The General Procedure for Fluorided Alumina Catalysts was followed using 19.0 g (30 mL) of $COCl_2/Al_2O_3$ (2% Co) as the initial catalyst charge. The $HCl:CH_2FCF_3$ (HFC-134a) molar ratio was varied from 0.5:1 to 5:1, the reaction temperature was varied from 150 to 430° C., and the contact time (C.T.) was varied from 10 to 30 seconds. The results of these runs are shown in Table 6.

TABLE 6

| Hrs. on Stream | T °C. | Molar Ratio | C.T. Sec. | % 134a[a] | % 1122[b] | % 133a[c] | % 1121 | % 1120[d] |
|---|---|---|---|---|---|---|---|---|
| 2.0 | 350 | 2:1 | 10 | 13.2 | 0.4 | 70.4 | 1.7 | 12.5 |
| 4.0 | 350 | 1:1 | 10 | 27.2 | 0.4 | 67.1 | 1.0 | 3.1 |
| 6.0 | 350 | 0.5:1 | 15 | 35.6 | 0.4 | 62.9 | 0.2 | 0.2 |
| 9.0 | 310 | 1:1 | 10 | 60.1 | 0.0 | 33.1 | 2.3 | 3.6 |
| 12.0 | 250 | 1:1 | 10 | 88.3 | 0.0 | 9.5 | 0.8 | 0.4 |
| 14.0 | 250 | 2:1 | 10 | 88.3 | 0.0 | 9.5 | 0.7 | 0.5 |
| 16.0 | 310 | 2:1 | 10 | 67.9 | 0.2 | 25.7 | 2.6 | 2.7 |
| 19.0 | 350 | 2:1 | 10 | 29.3 | 0.4 | 53.2 | 3.0 | 13.1 |
| 24.0 | 410 | 2:1 | 10 | 9.7 | 2.6 | 62.7 | 5.5 | 19.0 |
| 27.0 | 430 | 2:1 | 30 | 4.3 | 4.1 | 60.7 | 7.7 | 18.4 |
| 31.0 | 350 | 2:1 | 30 | 20.1 | 0.4 | 65.1 | 2.3 | 11.2 |
| 41.0 | 150 | 2:1 | 30 | 97.2 | 0.0 | 1.8 | 0.0 | 0.0 |
| 53.0 | 290 | 5:1 | 30 | 61.1 | 0.1 | 32.4 | 2.4 | 3.2 |
| 56.0 | 350 | 5:1 | 30 | 12.7 | 0.5 | 53.8 | 4.3 | 27.1 |
| 59.0 | 410 | 5:1 | 30 | 1.5 | 1.8 | 35.5 | 8.4 | 50.8 |

[a]134a is $CH_2FCF_3$
[b]1122 is $CHCl=CF_2$
[c]133a is $CH_2ClCF_3$
[d]1120 is $CHCl=CCl_2$

Example 7

Reaction of $CH_2FCF_3$ and HCl

The reactor, catalyst, and catalyst treatment were the same as those described in Example 2 above. The reactor was then brought back to the desired operating temperature, and flow of reactants started. The $CH_2FCF_3$ (HFC-134a)/HCl molar ratio was 1/5, the contact time was 30 seconds and the reaction temperatures were as shown in Table 7.

TABLE 7

| Hrs. on Stream | T ° C | % 134a | % 133a | % 1120 |
|---|---|---|---|---|
| 3 | 100 | 95.7 | 4.3 | <0.1 |
| 10 | 150 | 66.0 | 33.1 | 0.7 |
| 16 | 200 | 13.0 | 85.3 | 1.4 |
| 20 | 240 | 0.2 | 93.9 | 5.3 |

Example 8

Reaction of $CHClFCF_3$ and HCl

The reactor, catalyst, and catalyst treatment were the same as those described in Example 2 above. The reactor was then brought back to the desired operating temperature, and flow of reactants started. The $CHClFCF_3$ (HCFC-124)/HCl molar ratio was 1/5, the contact time was 30 seconds and the reaction temperatures were as shown in Table 8.

TABLE 8

| Hrs. on Stream | T ° C. | % 125 | % 115 | % 124 | % 133a | % 114a | % 123 | % 1111 | % 1120 | % PCE |
|---|---|---|---|---|---|---|---|---|---|---|
| 4 | 160 | 0.0 | 0.0 | 89.4 | 0.0 | 0.0 | 10.3 | 0.0 | 0.0 | 0.0 |
| 6 | 200 | 0.1 | 0.0 | 56.7 | 0.0 | 0.0 | 42.8 | 0.0 | 0.0 | 0.0 |
| 9 | 260 | 1.4 | 0.0 | 10.4 | 0.0 | 0.0 | 85.8 | 0.1 | 0.0 | 1.9 |
| 12 | 320 | 7.4 | 0.1 | 11.1 | 0.6 | 0.8 | 55.9 | 1.0 | 0.8 | 21.7 |
| 14 | 360 | 10.3 | 5.5 | 6.8 | 2.9 | 3.9 | 21.2 | 2.6 | 6.1 | 37.8 |

Example 9

Reaction of $CHCl_2CF_3$ and HCl

The reactor, catalyst, and catalyst treatment were the same as those described in Example 2 above. The reactor was then brought back to the desired operating temperature, and flow of reactants started. The $CHCl_2CF_3$ (HCFC-123)/HCl molar ratio was 1/5, the contact time was 30 seconds and the reaction temperatures were as shown in Table 9.

TABLE 9

| Hrs. on Stream | T °C. | % 125 | % 115 | % 124 | % 133a | % 114a | % 123 | % 1111 | % 1120 | % PCE |
|---|---|---|---|---|---|---|---|---|---|---|
| 8  | 240 | 0.0 | 0.0  | 0.6 | 0.0 | 0.0 | 97.0 | 0.0 | 0.0  | 2.1  |
| 11 | 300 | 0.1 | 0.0  | 2.9 | 0.0 | 0.0 | 83.6 | 0.3 | 0.2  | 12.6 |
| 14 | 360 | 4.4 | 2.1  | 4.8 | 1.0 | 2.6 | 20.5 | 2.9 | 4.7  | 55.1 |
| 16 | 400 | 1.2 | 13.3 | 1.1 | 0.9 | 2.4 | 4.3  | 3.7 | 13.9 | 56.1 |

Example 10

Reaction of $CHF_3$ and HCl

A reactor (a 0.5 inch (1.3 cm) ID, 12 inch (30.5 cm) long Inconel™ nickel alloy pipe) was charged with 39.0 g (30 mL) of chrome oxide catalyst and placed in a sand bath. The bath was gradually heated to 175° C. while $N_2$ gas at a flow rate of 50 cc/min was passed through the reactor to remove traces of water. After 2.5 hours, the nitrogen flow was stopped and HCl was passed through the reactor for 4.5 hours while gradually raising the reactor temperature to 425° C. At this point the temperature was reduced to 250° C. while passing HCl through the catalyst bed for an additional 15 minutes. Following this, the HCl flow was stopped and nitrogen passed over the catalyst overnight at about 250° C. Thereafter, the nitrogen flow was stopped and the reactant flows started.

The $HCl:CHF_3$ (HFC-23) molar ratio was varied from 2:1 to 20:1, the reaction temperature was varied from 250 to 350° C., and the contact time was 30 seconds. The results of these runs are shown in Table 10.

Example 11

Reaction of $CHF_3$ and HCl

A reactor (a 0.5 inch (1.3 cm) ID, 12 inch (30.5 cm) long Inconel™ nickel alloy pipe) was charged with 19.1 g (30 mL) of gamma-alumina and placed in a sand bath. The bath was gradually heated to 175° C. while $N_2$ gas at a flow rate of 50 cc/min was passed through the reactor to remove traces of water. After 2.5 hours, the nitrogen flow was stopped and HF was passed through the reactor for 4.5 hours while gradually raising the reactor temperature to 425° C. At this point the temperature was reduced to 250° C. while passing HF through the catalyst bed for an additional 15 minutes. Following this, the HF flow was stopped and nitrogen passed over the catalyst overnight at about 250° C. Thereafter, the nitrogen flow was stopped and the reactant flows started.

The $HCl:CHF_3$ (HFC-23) molar ratio was varied from 10:1 to 20:1, the reaction temperature was varied from 275 to 350° C., and the contact time was 30 seconds. The results of these runs are shown in Table 11.

TABLE 10

| Hrs. on Stream | T °C. | Molar Ratio | % 23[a] | % 13[b] | % 40[c] | % 22[d] | % 21[e] | % 30[f] | % 20[g] |
|---|---|---|---|---|---|---|---|---|---|
| 1.5 | 250 | 10:1 | 99.5 | 0.0 | 0.3 | 0.1 | 0.0 | 0.0 | 0.0 |
| 5.5 | 300 | 20:1 | 79.4 | 0.2 | 1.9 | 3.8 | 1.3 | 1.0 | 12.3 |
| 6.0 | 325 | 2:1  | 94.9 | 0.2 | 1.2 | 2.2 | 0.7 | 0.2 | 0.7 |
| 6.5 | 325 | 5:1  | 91.6 | 0.3 | 2.0 | 3.0 | 0.5 | 0.5 | 2.1 |
| 7.0 | 325 | 10:1 | 85.9 | 0.5 | 1.6 | 3.9 | 1.1 | 0.6 | 6.3 |
| 9.5 | 350 | 20:1 | 69.8 | 2.5 | 0.3 | 5.3 | 2.4 | 1.6 | 18.1 |

[a]23 is $CHF_3$
[b]13 is $CClF_3$
[c]40 is $CH_3Cl$
[d]22 is $CHClF_2$
[e]21 is $CHCl_2F$
[f]30 is $CH_2Cl_2$
[g]20 is $CHCl_3$

TABLE 11

| Hrs. on Stream | T °C. | Molar Ratio | % 23 | % 13 | % 22 | % 21 | % 20 |
|---|---|---|---|---|---|---|---|
| 0.5  | 275 | 10:1 | 84.1 | 0.0 | 3.3 | 1.2 | 11.3 |
| 5.5  | 300 | 10:1 | 82.1 | 0.0 | 4.7 | 1.6 | 11.5 |
| 8.0  | 325 | 20:1 | 71.0 | 0.1 | 5.6 | 2.2 | 21.0 |
| 10.0 | 350 | 20:1 | 68.4 | 0.2 | 5.8 | 2.6 | 23.0 |

Example 12

Chlorination of $CHCl_2CF_3$

The reactor and catalyst were the same as those used in Example 11. The $Cl_2$:HCFC-123:HCl molar ratio was 2:1:5, the reaction temperature was varied from 275 to 325° C., and the contact time was 30 seconds. The results of these runs are shown in Table 12.

TABLE 12

| T ° C. | % 115 | % 114 | % 114a | % 123 | % 113 | % 113a | % 112/a | % 111 | % PCE |
|---|---|---|---|---|---|---|---|---|---|
| 275 | 0.2 | 0.5 | 12.7 | 22.5 | 2.0 | 46.7 | 7.7 | 1.2 | 3.5 |
| 300 | 1.0 | 1.4 | 16.0 | 2.1 | 2.5 | 59.5 | 9.3 | 1.7 | 4.8 |
| 325 | 3.3 | 1.9 | 15.8 | 0.0 | 2.5 | 55.8 | 10.5 | 2.1 | 6.2 |

Example 13

Chlorination of $CH_2ClCF_3$

A reactor (a 0.5 inch (1.3 cm) ID, 12 inch (30.5 cm) long Inconel™ nickel alloy pipe) was charged with 23.6 g (30 mL) of aluminum fluoride catalyst and placed in a sand bath. The bath was gradually heated to 176° C. while $N_2$ gas at a flow rate of 50 cc/min was passed through the reactor. After 28 minutes, the nitrogen flow was stopped and HF was passed through the reactor for 2.0 hours while gradually raising the reactor temperature to about 400° C. At this point the temperature was reduced to 280° C. while passing HF through the catalyst bed for an additional 55 minutes. Following this, the HF flow was stopped and nitrogen passed over the catalyst until the temperature was 200° C. Thereafter, the nitrogen flow was stopped and the reactant flows started.

The $Cl_2$:HCFC-133a:HCl molar ratio was 4:1:20, the reaction temperature was varied from 250 to 350° C., and the contact time was 30 seconds. The results of these runs are shown in Table 13.

B. Catalyst Activation and Reaction

The reactor (a 0.5 inch (1.3 cm) ID, 12 inch (30.5 cm) long Inconel™ nickel alloy pipe) was charged with 13.6 g (30 mL) of Zn—$Al_2O_3$/graphite catalyst and placed in a sand bath. The bath was gradually heated to about 400° C. while $N_2$ gas at a flow rate of 50 cc/min. was passed through the reactor for about 2.5 hrs. The catalyst bed was then cooled under nitrogen over 1.5 hours to about 175° C. At that time in addition to nitrogen, HF was passed through the catalyst bed at 50 cc/min. After a few minutes at these conditions, a temperature rise to about 200° C. was observed. After an hour the temperature had decreased to about 175° C. whereupon the nitrogen flow was reduced to 20 cc/min. and the HF flow increased to 80 cc/min. Over 2.5 hours the bath temperature was gradually increased to about 340° C. At this point an increase in the catalyst bed temperature to 372° C. was observed. During the next 0.75 hour the bath temperature was gradually increased to 390° C. with the catalyst bed temperature rising to 411° C. At this point the nitrogen flow was increased to 75 cc/min. and the HF flow decreased to 25 cc/min. During the next 0.75 hour the flows were gradually adjusted to 15 cc/min. nitrogen and 80

TABLE 13

| T ° C. | % 133a | % 114 | % 114a | % 123 | % 113 | % 113a | % 112/a | % 1112a | % 111 | % PCE |
|---|---|---|---|---|---|---|---|---|---|---|
| 250 | 70.9 | 0.0 | 0.1 | 5.7 | 0.8 | 0.3 | 7.9 | 1.8 | 3.2 | 8.3 |
| 275 | 46.3 | 0.0 | 0.2 | 10.9 | 4.5 | 1.2 | 20.8 | 1.2 | 4.1 | 9.7 |
| 300 | 16.9 | 0.0 | 1.2 | 16.2 | 11.3 | 6.9 | 30.5 | 1.9 | 3.8 | 10.2 |
| 325 | 1.0 | 0.2 | 9.7 | 12.3 | 8.2 | 29.3 | 24.1 | 1.6 | 3.5 | 9.4 |
| 350 | 0.6 | 0.6 | 14.3 | 2.4 | 3.8 | 48.1 | 14.3 | 0.6 | 3.2 | 11.1 |

Example 14

Chlorination of $CHCl_2CF_3$

A. Catalyst Preparation

Samples of powdered gamma-alumina and graphite were dried overnight at 110° C. The dried, powdered gamma-alumina (100 g) was mixed with the dried graphite (96 g). A solution containing $ZnCl_2$ (4.6 g) in water (175 mL) was added to the mixture. The mixture was kneaded well after an additional 20 mL of water was added. After drying overnight at 100° C., the sample was granulated to 20/40 mesh (0.84/0.42 mm). Chemical analysis showed a Zn/Al ratio of 0.016. The surface area was 116 m2/g as measured by nitrogen adsorption.

cc/min. HF and both the bath and catalyst temperature were about 400° C. Following this, the HF flow was stopped and nitrogen passed over the catalyst until the temperature was 300° C. Thereafter, the nitrogen flow was stopped and the reactant flows started. The $Cl_2$:HCFC-123:HCl molar ratio was 2:1:5, the reaction temperature was varied from 275 to 325° C., and the contact time was 30 seconds. The results of these runs are shown in Table 14.

TABLE 14

| T ° C. | % 115 | % 114 | % 114a | % 123 | % 113 | % 113a | % 112/a[a] | % 1111 | % 111 | % PCE |
|---|---|---|---|---|---|---|---|---|---|---|
| 275 | 0.0 | 0.0 | 0.4 | 90.7 | 1.4 | 1.5 | 4.1 | 0.0 | 0.3 | 0.9 |
| 300 | 0.1 | 0.6 | 4.5 | 60.0 | 6.8 | 9.8 | 13.9 | 0.2 | 0.8 | 1.6 |
| 325 | 3.5 | 2.0 | 16.2 | 0.4 | 3.0 | 55.3 | 11.0 | 1.3 | 1.8 | 5.3 |

[a]112/a is $CCl_3CClF_2$ and $CCl_2FCCl_2F$

Example 15

Reaction of $CH_3CF_3$ and HCl

A reactor (a 0.5 inch (1.3 cm) ID, 12 inch (30.5 cm) long Inconel™ nickel alloy pipe) was charged with 49.0 g (30 mL) of acid washed silicon carbide (14–20 mesh, 12. mm–0.83 mm) and placed in a sand bath. The bath was gradually heated to 350° C. while $N_2$ gas at a flow rate of 50 cc/min was passed through the reactor. At this point the nitrogen flow was stopped and the reactants were passed through the reactor.

The $CH_3CF_3$:HCl molar ratio was 1:4, the reaction temperature was varied from 350° C. to 375° C., and the contact time (C.T.) was 30 seconds. The results of these runs are shown in Table 15.

TABLE 15

| T ° C. | % 1132a[a] | % 143a[b] | % 1131a[c] | % 142b[d] | % 141b[e] | % 113a[f] | TCE[g] | % 130a[h] |
|---|---|---|---|---|---|---|---|---|
| 350 | 0.7 | 92.8 | 1.7 | 1.2 | 0.2 | 2.8 | 0.3 | 0.3 |
| 375 | 1.3 | 89.6 | 2.7 | 1.7 | 0.4 | 3.6 | 0.2 | 0.3 |

[a]1132a is $CH_2=CF_2$
[b]143a is $CH_3CF_3$
[c]1131a is $CH_2=CClF$
[d]142b is $CH_3CClF_2$
[e]141b is $CH_3CCl_2F$
[f]1130a is $CH_2=CCl_2$
[g]TCE is $CHCl=CCl_2$
[h]130a is $CCl_3CH_2Cl$

It is understood that the invention is not confined to the particular formulations and examples herein illustrated, but it embraces such modified forms thereof as come within the scope of the following claims.

What is claimed is:

1. A method for reducing the fluorine content of an acyclic saturated compound selected from the group consisting of $CHCl_2F$, $CHClF_2$, $CHF_3$, $CHClFCF_3$, $CHCl_2CF_3$, and $CHF_2CH_3$, comprising the step of
reacting said acyclic saturated compound with HCl in the vapor phase at a temperature within the range of from about 250° C. to 450° C. in the presence of a catalyst, the mole ratio of HCl to said acyclic saturated compound being at least about 1:1.

2. The method of claim 1 wherein the molar ratio of HCl to the acyclic saturated compound is from 2:1 to 5:1, and the acyclic saturated compound is reacted with HCl at a temperature less than about 350° C. to produce compounds of reduced fluorine content which are primarily saturated compounds.

3. The method of claim 1 wherein the catalyst comprises aluminum fluoride.

4. The method of claim 1 wherein the catalyst comprises chromium oxide.

5. The method of claim 1 wherein the catalyst is selected from alumina, fluorided alumina, magnesium fluoride on aluminum fluoride, alumina on carbon, aluminum fluoride on carbon, and fluorided alumina on carbon.

6. The method of claim 1 wherein the catalyst comprises a metal selected from the group consisting of chromium, zinc, Group VIII metals, Group VIIB metals, Group IIIB metals, Group IB metals, and metals having an atomic number of 58 through 71.

7. The method of claim 6 wherein the metal is on alumina, aluminum fluoride, fluorided alumina or carbon; and wherein the total metal content is from about 0.1 to 20 percent by weight.

8. The method of claim 1 wherein $Cl_2$ is present during the reaction and a perhalogenated product is produced.

9. A method for reducing the fluorine content of an acyclic saturated compound selected from the group consisting of $CHCl_2F$, $CHClF_2$ and $CHF_3$, comprising the step of:
reacting said acyclic saturated compound with HCl in the vapor phase at a temperature within the range of from about 250° C. to 450° C. in the presence of a catalyst, the mole ratio of HCl to said acyclic saturated compound being at least about 1:1.

10. The method of claim 9 wherein the acyclic saturated compound is $CHCl_2F$.

11. The method of claim 9 wherein the acyclic saturated compound is $CHClF_2$.

12. The method of claim 9 wherein the acyclic saturated compound is $CHF_3$.

13. The method of claim 1 wherein the acyclic saturated compound is $CHClFCF_3$.

14. The method of claim 1 wherein the acyclic saturated compound is $CHCl_2CF_3$.

15. The method of claim 1 wherein the acyclic saturated compound is $CHF_2CH_3$.

16. A method for reducing the fluorine content of an acyclic saturated compound of the formula $CF_aX_bH_c$ wherein each X is independently selected from the group consisting of chlorine and bromine, and wherein a is 1 to 3, b is 0 to 2, c is 1 to 3 and a+b+c equals 4, comprising the step of:
reacting said acyclic saturated compound with HCl in the vapor phase at a temperature within the range of from about 250° C. to 450° C. in the presence of a catalyst, the mole ratio of HCl to said acyclic saturated compound being at least about 1:1.

* * * * *